United States Patent
Ishii

(10) Patent No.: US 6,540,698 B1
(45) Date of Patent: Apr. 1, 2003

(54) MEDICAL DEVICE HAVING WET LUBRICITY AND METHOD FOR ITS PRODUCTION

(75) Inventor: Naoki Ishii, Kanagawa (JP)

(73) Assignee: Terumo Kabushiki Kaisha, Tokyo (JP)

( * ) Notice: Subject to any disclaimer, the term of this patent is extended or adjusted under 35 U.S.C. 154(b) by 159 days.

(21) Appl. No.: 09/714,102

(22) Filed: Nov. 17, 2000

(30) Foreign Application Priority Data

Nov. 19, 1999 (JP) ............................................. 11-330420

(51) Int. Cl.$^7$ ............................ A61B 5/00; A61M 25/00
(52) U.S. Cl. ...................... 600/585; 600/435; 604/264; 623/1.11
(58) Field of Search ................................ 600/433–435, 600/585; 128/897, 898; 604/93.01, 96.01, 164.1, 164.11, 264, 265, 523; 623/1.1–2.1, 3.1; 523/105, 106, 112, 113, 201; 427/2.1, 2.24, 2.25, 402, 407.1, 412.1; 424/422, 423, 429; 428/36.91, 420–424.8; 528/904

(56) References Cited

U.S. PATENT DOCUMENTS

| | | | | |
|---|---|---|---|---|
| 5,441,488 A | * | 8/1995 | Shimura et al. | ............. 424/425 |
| 5,509,899 A | | 4/1996 | Fan et al. | |
| 5,670,558 A | | 9/1997 | Onishi et al. | |
| 5,756,144 A | * | 5/1998 | Wolff et al. | ................... 427/2.1 |
| 5,908,656 A | * | 6/1999 | Ishikawa et al. | ........ 264/173.19 |
| 6,080,488 A | | 6/2000 | Hostettler et al. | |

FOREIGN PATENT DOCUMENTS

| | | |
|---|---|---|
| JP | 4-249587 A | 9/1992 |
| JP | 5-043821 A | 2/1993 |
| JP | 10-130455 A | 5/1998 |
| WO | WO 00/71181 A1 | 11/2000 |

* cited by examiner

*Primary Examiner*—Max F. Hindenburg
*Assistant Examiner*—Charles Marmor, II
(74) *Attorney, Agent, or Firm*—Burns, Doane, Swecker & Mathis, LLP

(57) ABSTRACT

A highly safe medical device which exhibits long-lasting low surface friction in a body fluid or in an aqueous medium is provided. Also provided is a method for producing such medical device wherein substantially no limitation is imposed on the type of the substrate used, and the hydrophilic high molecular weight compound or the water-soluble or water-swellable high molecular weight compound responsible for the surface lubricity can be readily coated on the surface. In the present invention, a hydrophilic high molecular weight compound having at least one carbonyl group or hydrazine residue in the molecule and a cross-linking agent having at least two hydrazine residues or carbonyl groups in the molecule are reacted to thereby form a surface lubrication layer comprising the reaction product. In another embodiment, an interpenetrating network is formed between the reaction product of a compound having at least one carbonyl group or hydrazine residue in the molecule and a cross-linking agent, and a water-soluble or water-swellable high molecular weight compound to thereby form a surface lubrication layer.

17 Claims, No Drawings

MEDICAL DEVICE HAVING WET LUBRICITY AND METHOD FOR ITS PRODUCTION

BACKGROUND OF THE INVENTION

1. Field of the Invention

This invention relates to a medical device and its production method. More specifically, this invention relates to a medical device having a surface exhibiting excellent wet lubricity owing to the high molecular weight compound on the surface of the device, as well as its production method.

2. Prior Art

Materials used in producing catheters, guide wires and other medical devices should be capable of exhibiting surface lubricity since reduction in frictional resistance of the surface is critical for reducing tissue damage and improving the operational capability.

Typical methods that have been employed for reducing the surface frictional resistance include use of a material exhibiting reduced friction such as Teflon™ which is inherently provided with low friction, and coating of various oils on the surface of the substrate. These methods, however, suffered from insufficient reduction in the frictional resistance or insufficient retention of the lubricity.

Another method that has been employed for the surface lubrication is the lubrication by coating a hydrophilic polymer on the surface. Such coating is superior to the use of Teflon™ or oil coating as described above in the lubricity. However, it has been generally conceived that such coating is inferior in durability, and various methods have been proposed for improving the durability.

JP-B 59-19582, for example, discloses a surface-lubricating method wherein polyvinyl pyrrolidone (PVP) which is a hydrophilic polymer and isocyanate group which is a reactive functional group are used to form a network of chemical bond for immobilization of the PVP to the substrate surface. JP-B 59-193766 discloses a surface lubrication method by the reaction between polyethylene oxide (PEO) and isocyanate group. JP-B 1-55023 discloses a surface lubrication method wherein the surface is coated with a combination of a copolymer comprising two or more types of monomers having a functional group and isocyanate group.

These methods, however, utilized the reaction between a highly reactive proton-accepting functional group as represented by isocyanate and a proton-donating functional group, and a consequence, suffered from the problems of limitation of the solvent used to non-proton-donating organic solvents, complicated coating procedure, and necessity for a strict moisture control of the coating solution and the working area.

As an example of more recent technology, JP-A 10-5325 discloses a surface lubrication method using polyurethane emulsion wherein phenomenon of the reactivation of the once blocked isocyanate group (or carboxyl group) by temperature elevation is utilized. This reaction, however, requires a high reaction temperature, and use of this reaction in the surface lubrication is associated with a fair risk that the substrate may loose its physical properties that are primarily required for the substrate since the temperature of the substrate is also elevated.

In the method wherein the surface lubricity is realized by using a hydrophilic polymer, the hydrophilic polymer is generally immobilized on the surface of the substrate by the coating operation, and affinity of the coated surface with water is then improved by the step wherein the coated surface is brought in contact with water, for example, by immersing in water or contacting with steam. Such procedure has the merit that the surface lubricity is more quickly realized upon wetting. However, in the surface lubrication method, the solvent used for the coating is generally an organic solvent, and the step of contacting with water should be effected subsequent to and separately from the coating step. This results in the complicated production process and increased cost.

When a physiological activity such as anti-thrombogenicity is to be imparted with the surface in addition to the lubricity by using a water-soluble physiologically active substance such as heparin, the step of imparting the lubricity by coating the surface with a solution of a hydrophilic polymer in an organic solvent had be carried out separately from the step of imparting the physiological activity by treating the surface with a solution of the water-soluble physiologically active substance in an aqueous solvent since the water-soluble physiologically active substance is generally insoluble in an organic solvent. In other words, the step of imparting the lubricity and the step of imparting the physiological activity could not be completed in the same step, and there had been the problem of complicated procedure.

SUMMARY OF THE INVENTION

In view of the situation as described above, an object of the present invention is to obviate the problems as described above, and to provide a highly safe medical device which has been imparted with long lasting lubricity under moderate coating conditions without using the highly reactive proton-accepting functional group as represented by isocyanate group, and with no loss in the physical properties primarily required for the substrate of the medical device; and a method for producing such medical device.

Another object of the present invention is to provide a medical device which has been imparted with the surface lubricity in simplified procedure by conducing the step of contacting the surface with water and the step of coating the surface in the same step, and as a consequence, a medical device which has been imparted with the surface lubricity at a reduced cost; and a method for producing such medical device.

Further object of the present invention is to provide a medical device exhibiting stable lubricity and physiological activity wherein a water-soluble physiologically active substance such as heparin has been reliably immobilized on its surface in a reliable, simple coating operation simultaneously with the substance responsible for the lubricity; and a method for producing such medical device.

The objects as described above are attained by the present invention as summarized (1) to (15), below.

(1) A medical device having a surface exhibiting lubricity when wet wherein the medical device has a surface lubrication layer formed on a substrate constituting the medical device, and said surface lubrication layer comprises a reaction product of a hydrophilic high molecular weight compound having at least one carbonyl group in the molecule and a cross-linking agent comprising a hydrazide compound having at least two hydrazine residues in one molecule.

(2) A medical device having a surface exhibiting lubricity when wet wherein the medical device has a surface lubrication layer formed on a substrate constituting the medical device, and said surface lubrication layer comprises a reaction product of a hydrophilic high molecular weight compound having at least one hydrazine residue in the molecule and a cross-linking agent comprising a carbonyl group-containing compound having at least two carbonyl groups in one molecule.

(3) The medical device according to (1) or (2) wherein said surface lubrication layer further comprises a water-soluble or water-swellable high weight molecular substance.

(4) The medical device according to any one of (1) to (3) wherein said cross-linking agent is soluble in an aqueous solvent.

(5) A medical device having a surface exhibiting lubricity when wet wherein the medical device has a surface lubrication layer formed on a substrate constituting the medical device, and said surface lubrication layer has an interpenetrating network comprising a reaction product of a carbonyl group-containing compound having at least one carbonyl group in the molecule with a hydrazide compound having at least two hydrazine residues in one molecule and a water-soluble or water-swellable high molecular weight substance.

(6) A medical device having a surface exhibiting lubricity when wet wherein the medical device has a surface lubrication layer formed on a substrate constituting the medical device, and said surface lubrication layer has an interpenetrating network comprising a reaction product of a hydrazide compound having at least one hydrazine residue in the molecule with a carbonyl group-containing compound having at least two carbonyl groups in one molecule and a water-soluble or water-swellable high molecular weight substance.

(7) The medical device according to (5) or (6) wherein at least one of said hydrazide compound and said carbonyl group-containing compound is soluble in an aqueous solvent.

(8) The medical device according to any one of (1) to (7) wherein said surface lubrication layer further comprises a water-soluble physiologically active substance.

(9) A method for producing a medical device having a surface exhibiting lubricity when wet comprising the steps of, coating a surface of a substrate constituting the medical device with a solution containing a hydrophilic high molecular weight compound having at least one carbonyl group in the molecule, and coating the surface with a solution containing a cross-linking agent comprising a hydrazide compound having at least two hydrazine residues in one molecule.

(10) A method for producing a medical device having a surface exhibiting lubricity when wet comprising the steps of, coating a surface of a substrate constituting the medical device with a solution containing a hydrophilic high molecular weight compound having at least one hydrazine residue in the molecule, and coating the surface with a solution containing a cross-linking agent comprising a carbonyl group-containing compound having at least two carbonyl groups in one molecule.

(11) The method for producing a medical device according to (9) or (10) wherein at least one of said solution containing the hydrophilic high molecular weight compound and said solution containing the a cross-linking agent further comprises a water-soluble or water-swellable high molecular weight substance.

(12) The method for producing a medical device according to (9) to (11) wherein an aqueous solvent is used for the solvent of said cross-linking agent.

(13) The method for producing a medical device according to (12) wherein said solution of said cross-linking agent in said aqueous solvent further comprises a water-soluble physiologically active substance.

(14) A method for producing a medical device having a surface exhibiting lubricity when wet comprising the steps of:
coating a surface of a substrate constituting the medical device with a solution containing a carbonyl group-containing compound having at least one carbonyl group in the molecule, and
coating the surface with a solution containing a hydrazide compound having at least two hydrazine residues in one molecule;
wherein at least one of said solution containing the carbonyl group-containing compound and said solution containing the hydrazide compound further comprises a water-soluble or water-swellable high molecular weight substance.

(15) A method for producing a medical device having a surface exhibiting lubricity when wet comprising the steps of:
coating a surface of a substrate constituting the medical device with a solution containing a hydrazide compound having at least one hydrazine residue in the molecule, and
coating the surface with a solution containing a cross-linking agent comprising a carbonyl group-containing compound having at least two carbonyl groups in one molecule; wherein at least one of said solution containing the carbonyl group-containing compound and said solution containing the hydrazide compound further comprises a water-soluble or water-swellable high molecular weight substance.

DETAILED DESCRIPTION OF THE INVENTION

This invention relates to a medical device having a surface exhibiting lubricity when wet wherein said surface has been formed by reacting a hydrophilic high molecular weight compound having at least one hydrazine residue or carbonyl group and a cross-linking agent comprising a compound having at least two functional groups which are capable of reacting with the hydrazine residue or the carbonyl group on the surface of the substrate constituting the medical device to thereby form a surface lubrication layer by the reaction product. Namely, this invention relates to a medical device having a surface exhibiting lubricity when wet wherein the medical device has a surface lubrication layer formed on the substrate constituting the medical device, and said surface lubrication layer comprises a reaction product of a hydrophilic high molecular weight compound(A) having at least one selected from a group consisting of a carbonyl group and a hydrazine residue in the molecule and a cross-linking agent (B) having at least two carbonyl groups or hydrazine residues which are capable of reacting with the carbonyl group or the hydrazine residue in one molecule. This invention also relates to a method for producing such medical device.

This invention also relates to a medical device having a surface exhibiting lubricity when wet wherein said surface has a surface lubrication layer formed on the substrate constituting the medical device, and said surface lubrication layer has an interpenetrating network of a water-soluble or water-swellable high molecular weight substance(D) and a reaction product(C) comprising a carbonyl group-containing compound having at least one carbonyl group in the molecule with a hydrazide compound having at least two hydrazine residues in one molecule, or a hydrazide compound having at least one hydrazine residue in the molecule with a carbonyl group-containing compound having at least two carbonyl group in the molecule. This invention also relates to a method for producing such medical device.

The present invention utilizes cross-linking reaction between carbonyl group and hydrazine residue, and accordingly, a covalent bond is formed between the high molecular weight compound and the cross-linking agent through a reaction under moderate conditions. Firm insolubilization of the hydrophilic high molecular weight compound on the surface of the substrate is thereby enabled without detracting from the physical properties primarily required for the substrate of a medical device. Such reaction also allows use of a proton-donating solvent, and strict moisture control is no longer required in the working area during the reaction.

Next, the present invention is described for the embodiment wherein a surface lubrication layer is formed from the reaction product between the high molecular weight compound (A) and the cross-linking agent(B).

Combination of the high molecular weight compound (A) and the cross-linking agent (B) is not particularly limited when one is a hydrazide compound having a hydrazine residue and the other is a carbonyl group-containing compound. When working conditions or the odor during the reaction is taken into consideration, it is preferable to use a carbonyl group-containing compound for the hydrophilic high molecular weight compound(A) and a hydrazide compound having two or more hydrazine residues in one molecule for the cross-linking agent(B).

The hydrophilic high molecular weight compound(A) used in the present invention is a high molecular weight compound which has at least one functional group (hydrazine residue or carbonyl group) in the molecule, said functional group being capable of reacting with a cross-linking agent having two or more functional groups; and which swells or dissolves upon moisture absorption. When such hydrophilic high molecular weight compound is immersed in an aqueous medium such as physiological saline, a buffer, or blood, the compound swells by absorbing the water and the absorbed water imparts lubricity with the surface of the medical device upon contact of the medical device with, for example, the inner wall of a body cavity such as blood vessel. In view of such situation, the hydrophilic high molecular weight compound may preferably have a water absorption of 50% by weight or higher, and preferably, a water absorption of 100% by weight or higher against own weight at the working temperature range (usually in the range of 30 to 40° C.) in order to realize a sufficient lubricity.

The hydrophilic high molecular weight compound (A) is not limited for its molecular weight. However, the average molecular weight is preferably in the range of 2,000 to 5,000,000 and more preferably, in the range of 20,000 to 2,000,000.

The hydrophilic high molecular weight compound(A) used is preferably a copolymer having a hydrophilic unit (A-1) which is responsible for the lubricity and a reactive unit (A-2) having a reactive functional group (hydrazine residue or carbonyl group). The type of the hydrophilic copolymer used is not particularly limited, and the hydrophilic copolymer is preferably a block copolymer or a graft copolymer in view of lubricity while the hydrophilic copolymer is preferably a random copolymer having dispersed cross-linking point in view of the film strength after completion of the cross-linking. A suitable type, however, should be adequately selected depending on the physical properties required for the resulting film.

In the hydrophilic copolymer as described above, the hydrophilic unit(A-1) responsible for the lubricity may comprise 90 parts by weight, preferably 95 parts by weight, and more preferably 98 parts by weight of the hydrophilic copolymer.

Such hydrophilic copolymer can be produced by copolymerizing a reactive monomer(A-2) having hydrazine residue or carbonyl group in the molecule and a hydrophilic monomer(A-1); or by copolymerizing a reactive monomer having a reactive functional group other than the hydrazine residue or the carbonyl group which can be further converted into the hydrazine residue or the carbonyl group and a hydrophilic monomer (A-1), and then converting the reactive functional group into the hydrazine residue or the carbonyl group. The reactive monomer constitutes the reactive unit having the reactive functional group in the hydrophilic copolymer, while the hydrophilic monomer constitutes the hydrophilic (lubricity) unit which is responsible for the lubricity of the hydrophilic copolymer.

The hydrophilic monomer(A-1) used is not limited to any particular type as long as it realizes lubricity in a body fluid or an aqueous medium. Preferable examples of such hydrophilic monomer include those containing as their main component a water-soluble monomer such as acrylamide or it derivative, vinylpyrrolidone, and acrylic acid, methacrylic acid or its derivative. Examples are acrylamide and its derivatives such as acrylamide, N-methylacrylamide, N,N-dimethylacrylamide, acryloylmorpholine, and N,N-dimethylaminoethylacrylate; vinylpyrrolidone, 2-methacryloyloxyethyl-D-glycoside, 2-methacryloyloxyethyl-D-mannoside, methyl vinyl ether, and maleic anhydride-based high molecular weight substances such as methyl vinyl ether-maleic anhydride copolymer and its partial alkylester. Among these, the preferred in view of the ease of synthesis and handling convenience are acrylamide and acrylamide derivatives such as dimethylacrylamide, maleic anhydride-based high molecular weight substances, and methyl vinyl ether. The maleic anhydride-based high molecular weight substances are not limited to those which are water-soluble, and also included are those which have been insolubilized as long as the maleic anhydride-based high molecular weight substances are the main component. The hydrophilic monomer used is most preferably the one containing dimethylacrylamide as its main component.

The reactive monomer(A-2) used is not limited to any particular type as long as it is a monomer capable of forming a unit containing carbonyl group or a unit containing hydrazine residue in the hydrophilic copolymer. Exemplary such monomers include those containing a carbonyl group or hydrazine residue, and the monomers containing a functional group other than the carbonyl group and the hydrazine residue which can be converted into the carbonyl group or the hydrazine residue. Such conversion of the functional group may also take place after the copolymerization with the hydrophilic monomer.

The reactive monomer (A-2) containing carbonyl group used is not limited to any particular type as long as it contains at least one carbonyl group in one molecule. The preferable monomers, however, are those having a polymerizable double bond. Exemplary such monomers include diacetone acrylamide, diacetone methacrylamide, and vinyl alkyl ketone. The most preferred is diacetone acrylamide.

The reactive monomer(A-2) containing hydrazine residue used is not limited to any particular type as long as it contains at least one hydrazine residue in one molecule and it is polymerizable. Exemplary preferable monomers are those wherein carboxylate group in an ester of an unsaturated acid having a polymerizable double bond such as acrylic acid, methacrylic acid, itaconic acid, crotonic acid, and α chloroacrylic acid, and preferably, ester of an unsaturated acid with a lower alcohol has been converted into hydrazine residue by reaction with hydrazine or hydrazine hydrate. Examples of the monomer having a reactive functional group other than the hydrazine residue which can be further converted into the hydrazine residue include esters of an unsaturated acid having a polymerizable double bond such as acrylic acid, methacrylic acid, itaconic acid, crotonic acid, and α chloroacryl acid, and preferably, ester of an unsaturated acid with a lower alcohol. It is also preferable to produce the hydrophilic copolymer by copolymerizing such monomer with the hydrophilic monomer, and then treating the carboxylate group in the copolymer for conversion into the hydrazine or the hydrazine residue.

Polymerization of such monomers can be induced by heating, photo- or radiation energy, and initiated with a polymerizing catalyst such as a radical initiator, for example, peroxide such as benzoyl peroxide(BPO), azo compound such as azobisisobutyronitrile(AIBN), peroxosulfate, redox catalyst comprising peroxide and reducing reagent, and organometallic compound-oxygen. Polyperoxide(PPO) having two or more peroxide groups in one molecule can also be used for the polymerizing catalyst(initiator).

Solution polymerization may preferably be applied in using of solvent such as dioxane.

In the present invention, the cross-linking agent(B) which is reactive with the hydrophilic high molecular weight compound is a hydrazide compound having at least two hydrazine residues in one molecule when the hydrophilic high molecular weight compound is a carbonyl group-containing compound, and carbonyl group-containing compound having at least two carbonyl groups in one molecule when the hydrophilic high molecular weight compound is a hydrazine residue-containing compound. Such cross-linking agent(B) forms a covalent bond through reaction with the carbonyl group or the hydrazine residue of the hydrophilic high molecular weight compound(A), and the reaction product (cross-linked product) is insolubilized on the surface of the substrate constituting the medical device. The hydrophilic high molecular weight compound (A) is thereby firmly immobilized on the surface of the substrate constituting the medical device.

Such cross-linking agent (B) is used at an amount of 0.01 to 1.5 moles, and preferably, at an amount of 0.1 to 1.0 mole per 1 mole of the functional group of the hydrophilic copolymer.

Furthermore, the cross-linking agent(B) is preferably the one which is soluble in an aqueous solvent (i.e. which is water-soluble). Use of such cross-linking agent (B) enables use of an aqueous solvent for its dissolution, and working conditions including the odor will be improved during the reacting of the solution containing the cross-linking agent (B) with the hydrophilic high molecular weight compound (A) coated on the surface of the substrate. Use of an aqueous solvent also imparts the resulting lubricating surface layer with affinity to water simultaneously or concurrent with the reaction between the hydrophilic high molecular weight compound(A) and the cross-linking agent(B), and a separate step of contacting the surface with water can be omitted to result in the simplified surface lubricating steps. Furthermore, use of an aqueous solvent enables simultaneous incorporation of the water-soluble physiologically active substance as described below with the cross-linking agent(B), and a surface having physiological activity in addition to the wet surface lubricity can be realized at once in the step necessary for the surface lubrication.

In the present invention, a hydrazide compound having at least two hydrazine residues in the molecule is used for the cross-linking agent(B) when the hydrophilic high molecular weight compound (A) used is a carbonyl group-containing compound. Exemplary such hydrazide compounds include hydrazide compounds such as carbohydrazide, adipic dihydrazide, and 1,3-bis (hydrazinocarboethyl)-5-isopropylhydantoin; a polymer or a copolymer produced by treating poly(meth)acrylate to contain the hydrazine residue after its polymerization; and a polymer or a copolymer of a monomer which has been treated in the stage of the monomer to contain the hydrazine residue. Among these, the most preferred in terms of the reactivity and the purification process is carbohydrazide which is readily soluble in water.

In the present invention, a carbonyl group-containing compound having at least two carbonyl groups in the molecule is used for the cross-linking agent (B) when the hydrophilic high molecular weight compound (A) is a hydrazine residue-containing compound. Exemplary such carbonyl group-containing compounds include compounds such as glyoxal, butanedione, 2,4-pentanedione, diacetone acrylamide, diacetone methacrylamide, and vinyl alkyl ketone; and a polymer or a copolymer prepared by (co) polymerizing a carbonyl group-containing polymerizable monomer such as diacetone acrylamide, diacetone methacrylamide, and vinyl alkyl ketone.

In the present invention, a solution of the hydrophilic high molecular weight compound (A) in the solvent and a solution of the cross-linking agent(B) in the solvent are separately prepared. The solution containing the hydrophilic high molecular weight compound(A) is first coated on the surface of the substrate constituting the medical device, and then contacted(coated) with the solution containing the cross-linking agent(B) to promote the cross-linking reaction between the hydrophilic high molecular weight compound (A) and the cross-linking agent(B) to thereby insolubilize the reaction product (the cross-linked product) on the substrate surface and firmly immobilize the hydrophilic high molecular weight compound(A) on the substrate surface. As a consequence, the medical device exhibits lubricity when it is brought in contact with an aqueous medium such as a body fluid and physiological saline.

It should be noted that, in the present invention, when the hydrophilic high molecular weight compound (A) can be firmly immobilized on the face of the substrate and exhibits lubricity, a solution prepared from both the hydrophilic high molecular weight compound(A) and the cross-linking agent (B) may be applied on the face of the substrate.

The solvent used for the dissolution of the hydrophilic high molecular weight compound(A) and the solvent used for dissolution of the cross-linking agent (B) are not particularly limited, and the solvent can be adequately selected depending on the type of the material constituting the substrate of the medical device from the solvents including the proton-donating solvents which could not be employed in conventional reactions involving the isocyanate. For example, an organic solvent containing water can be used for dissolution of the hydrophilic high molecular weight compound(A) and the cross-linking agent(B), and the substrate surface can be coated with the solution to promote the cross-linking reaction. However, for stronger immobilization of the hydrophilic high molecular weight compound(A) to the substrate surface, the solvent for dissolution of the hydrophilic high molecular weight compound(A) is preferably selected from the solvents which is capable of swelling the substrate. Use of such solvent enables impregnation of the hydrophilic high molecular weight compound(A) in the substrate and firm immobilization of the hydrophilic high molecular weight compound (A) in the substrate. On the other hand, the solvent used for dissolution of the cross-linking agent (B) is preferably a solvent which does not substantially swell the substrate.

It should be noted that, when the material constituting the substrate is a material which is not swelled by the solvent, effects equivalent to the use of a swellable solvent can be achieved by the procedure wherein the hydrophilic high molecular weight compound (A) dispersed in a polymer which has no functional group reactive with the carbonyl group and hydrazine residue of hydrophilic high molecular weight compound(A) or the cross-linking agent(B) that is soluble in the solvent is coated on t-he substrate surface, and the cross-linking agent(B) is thereafter reacted with the hydrophilic high molecular weight compound(A), or, when the hydrophilic high molecular weight compound used is the hydrophilic copolymer as described above, by incorporating a monomer (structural unit) which has high affinity for the material constituting the substrate in the copolymer.

Such polymer includes a polyurethane such as 'PANDEX T-5210' manufactured by Dainippon Ink & Chemicals, Inc.

The conditions for the reaction between the hydrophilic high molecular weight compound(A) and the cross-linking agent (B) are not particularly limited as long as the pH of the reaction system is on the acidic side (pH<7) since the reaction is promoted in such range, and the pH is preferably adjusted to the range of up to 5, and more preferably, to the range of up to 3 for completion of the cross-linking reaction in a short period. On the other hand, use of a solution having a pH near 7 is preferable for the handling convenience of the solution, and in addition, the copolymer used in the reaction is preferably a copolymer which preliminarily contains an anionic monomer such as acrylic acid. These reaction conditions are not particularly limited, and the reaction conditions should be adequately selected depending on the pH of the reaction system, the specific procedure employed, and the reaction time.

In the present invention, a water-soluble or water-swellable high molecular weight substance may be further incorporated in the surface lubrication layer as described above. The water-soluble or water-swellable high molecular weight substance is not limited to any particular type as long-as it exhibits lubricity when brought in contact with an aqueous medium such as a body fluid or physiological saline, and preferable examples of such substances are polyvinyl pyrrolidone, poylethylene glycol, maleic anhydride-based high molecular weight compound such as maleic anhydride-methyl vinyl ether copolymer, and sodium polyacrylate. These compound are also described as the water-soluble or water-swellable high molecular weight substance(D) below.

The water-soluble or water-swellable high molecular weight substance may preferably form an interpenetrating network with the reaction product (cross-linked product) of the hydrophilic high molecular weight compound(A) and the cross-linking agent (B) on the surface of the substrate. Such formation of the interpenetrating network enables firm immobilization of the water-soluble or water-swellable high molecular weight substance to the substrate surface. Such formation of the interpenetrating network can be accomplished by incorporating the water-soluble or water-swellable high molecular weight substance in at least one of the solution containing the hydrophilic high molecular weight compound (A) and the solution containing the cross-linking agent(B).

The method for incorporating the water-soluble or water-swellable high molecular weight substance in the surface lubrication layer is not limited to the formation of the interpenetrating network as described above. Such incorporation may be accomplished, for example, by binding the water-soluble or water-swellable high molecular weight substance with the reaction product between the hydrophilic high molecular weight compound(A) and the cross-linking agent (B) through the reactive functional group in the reaction product; or by reacting the hydrophilic high molecular weight compound (A) and the cross-linking agent (B) to form the reaction product, and then coating a solution containing the water-soluble or water-swellable high molecular weight substance on the substrate surface for impregnation to thereby incorporate the water-soluble or water-swellable high molecular weight substance in the surface lubrication layer.

Next, the present invention is described in detail for the embodiment wherein an interpenetrating network is formed between the reaction product(C) of the carbonyl group-containing compound and the hydrazide compound with the water-soluble or water-swellable high molecular weight substance(D) to form the surface lubrication layer.

The carbonyl group-containing compound and the hydrazide compound used in the present invention are not particularly limited as long as they undergo the reaction to form the reaction product(cross-linked product)(C) comprising a high polymer network. However, for sufficient formation of the high polymer network, the carbonyl group-containing compound and the hydrazide compound are preferably a combination of a high molecular weight compound(C-1) of substantial molecular weight having at least one carbonyl group or hydrazine residue in the molecule and a polyfunctional compound (C-2) having at least two carbonyl groups or hydrazine residues in the molecule which is capable of functioning as a cross-linking agent.

The high molecular weight compound(C-1) having at least one carbonyl group or hydrazine residue in the molecule is not limited for its average molecular weight. However, the average molecular weight is preferably in the range of 2,000 to 5,000,000, and more preferably, in the range of 20,000 to 2,000,000. When the molecular weight is below such range, formation of the interpenetrating network of the reaction product(cross-linked) with the water-soluble or water-swellable high molecular weight substance may become insufficient. On the other hand, when the molecular weight is in excess of such range, solubility in the solvent will be reduced, and coating of the substrate surface may become difficult.

The high molecular weight compound(C-1) used is preferably a copolymer comprising a unit having a hydrazine residue or carbonyl group and another unit. The type of the copolymer used is not particularly limited, and the copolymer may be a block copolymer, a random copolymer, or a graft copolymer.

Such copolymer can be produced by copolymerizing a monomer having hydrazine residue or carbonyl group in the molecule with another polymerizable monomer; or by copolymerizing a monomer having a reactive functional group other than the hydrazine residue or the carbonyl group which can be further converted into the hydrazine residue or the carbonyl group with another polymerizable monomer, and then converting the reactive functional group into the hydrazine residue or the carbonyl group.

The monomer containing carbonyl group used is not limited to any particular type as long as it contains at least one carbonyl group in one molecule. The preferable monomers, however, are those having a polymerizable double bond. Exemplary such monomers include diacetone acrylamide, diacetone methacrylamide, and vinylalkyl ketone. The most preferred is diacetone acrylamide.

The monomer containing hydrazine residue used is not limited to any particular type as long as it contains at least one hydrazine residue in one molecule and it is polymerizable. Exemplary preferable monomers are those wherein carboxylate group in an ester of an unsaturated acid having a polymerizable double bond such as acrylic acid, methacrylic acid, itaconic acid, crotonic acid, and α-chloroacryl acid, and preferably, ester of an unsaturated acid with a lower alcohol has been converted into hydrazine residue by reaction with hydrazine or hydrazine hydrate.

Examples of the monomer having a reactive functional group other than the hydrazine residue which can be further converted into the hydrazine residue include esters of an unsaturated acid having a polymerizable double bond such as methacrylic acid, itaconic acid, crotonic acid, and α-chloroacrylic acid, and preferably, ester of an unsaturated acid with a lower alcohol, and the copolymer containing hydrazine residue can be suitably produced by copolymerizing such monomer with another polymerizable monomer, and then treating the carboxylate group in the copolymer for conversion into the hydrazine or the hydrazine residue.

The monomer copolymerized with the hydrazine residue-containing monomer or the monomer having a reactive functional group other than the hydrazine residue which can be further converted into the hydrazine residue may be an unsaturated acid monomer having a polymerizable double bond such as acrylic acid, methacrylic acid, itaconic acid, crotonic acid, and α-chloroacrylic acid.

The polyfunctional compound(C-2) which has at least two carbonyl groups or hydrazine residues in the molecule reacts with the compound(C-1) having at least one carbonyl group or hydrazine residue in the molecule in the presence of the water-soluble or water-swellable high molecular weight substance(D) to form a covalent bond, and the reaction product (cross-linked product) forms an interpenetrating network with the water-soluble or water-swellable high molecular weight substance(D) on the surface of the substrate constituting the medical device to become insolubilized. The water-soluble or water-swellable high molecular weight substance(D) is thereby firmly immobilized on the surface of the substrate constituting the medical device.

Such polyfunctional compound (cross-linking agent) (C-2) is used at an amount of 0.01 to 1.5 moles, and preferably, at an amount of 0.1 to 1.0 mole per 1 mole of the functional group in the compound(C-1) having at least one carbonyl group or hydrazine residue in one molecule.

The polyfunctional compound(cross-linking agent) (C-2) is preferably the one which is soluble in an aqueous solvent (i.e. which is water-soluble). Use of such polyfunctional compound(C-2) enables use of an aqueous solvent for its dissolution, and working conditions including the odor will be improved during the coating of the solution containing the polyfunctional compound(C-2) on the surface of the substrate for reaction with the high molecular weight compound(C-1) and the hydrophilic high molecular weight compound(D). Furthermore, use of an aqueous solvent also imparts the resulting lubricating surface layer with affinity to water simultaneously or concurrent with the reaction between the carbonyl group and the hydrazine residue and the formation of the interpenetrating network with the water-soluble or water-swellable high molecular weight substance (D), and a separate step of contacting the surface with water can be omitted to result in the simplified surface lubricating steps. Furthermore, use of an aqueous solvent enables incorporation of the water-soluble physiologically active substance as described below simultaneously with the polyfunctonal compound (cross-linking agent)(C-2), and a surface having physiological activity in addition to the wet surface lubricity can be realized at once in the step necessary for the surface lubrication.

In the present invention, when a hydrazide compound having at least two hydrazine residues in the molecule is used for the polyfunctional compound(C-2) which is capable of functioning as a cross-linking agent, exemplary such hydrazide compounds are hydrazide compounds such as carbohydrazide, adipic dihydrazide, and 1,3-bis(hydrazinocarboethyl)-5-isopropylhydantoin; a polymer or a copolymer produced by treating poly(meth)acrylate to leave the hydrazine residue after its polymerization; and a polymer or a copolymer of a monomer which has been treated in the stage of the monomer to contain the hydrazine residue. Among these, the most preferred in terms of the reactivity and the purification process is carbohydrazide which is readily soluble in water.

In the present invention, when a carbonyl group-containing compound having at least two carbonyl groups in the molecule is used for the polyfunctional compound (C-2) which is capable of functioning as a cross-linking agent, exemplary such carbonyl group-containing compounds are compounds such as glyoxal, butanedione, 2,4-pentanedione, diacetone acrylamide, diacetone methacrylamide, and vinyl alkyl ketone; and a polymer or a copolymer prepared by (co)polymerizing a carbonyl group-containing polymerizable monomer such as diacetone acrylamide, diacetone methacrylamide, and vinyl alkyl ketone.

The water-soluble or water-swellable high molecular weight substance(D) used in the present invention is a compound which swells or dissolves through moisture absorption. When such water-soluble or water-swellable high molecular weight substance(D) is immersed in an aqueous medium such as physiological saline, a buffer, or blood, the compound swells by absorbing the water and the absorbed water imparts lubricity with the surface of the medical device, for example, upon contact of the medical device with the inner wall of a body cavity such as a blood vessel. In view of such situation, the water-soluble or water-swellable high molecular weight substance (D) may preferably have a water absorption of 50% by weight or higher, and preferably, a water absorption of 100% by weight or higher against own weight at the working temperature range (usually in the range of 30 to 40° C.) in order to realize a sufficient lubricity.

The water-soluble or water-swellable high molecular weight substance(D) should be a substance which forms an interpenetrating network with the reaction product (cross-linked product)(C) between the carbonyl group-containing compound and the hydrazide compound, and which does not undergo detachment, delamination, or dissolution in repeated abrasion in the living body, and accordingly, the water-soluble or water-swellable high molecular weight substance should be a substance having a substantial molecular weight. In view of such situation, the average molecular weight of the water-soluble or water-swellable high molecular weight substance (D) is preferably in the range of 2,000 to 5,000,000, and more preferably, in the range of 20,000 to 2,000,000. When the molecular weight is below such range, formation of the interpenetrating network of the water-soluble or water-swellable high molecular weight substance (D) with the reaction product (cross-linked product)(C) between the carbonyl group-containing compound and the hydrazide compound may become insufficient and risk of the detachment, delamination, or dissolution in the body will be increased. On the other hand, when the molecular weight is in excess of such range, solubility of the water-soluble or water-swellable high molecular weight substance(D) in the solvent will be reduced, and coating of the substrate surface may become difficult.

Preferable examples of the water-soluble or water-swellable high molecular weight substance(D) are polyvinyl pyrrolidone, poylethylene glycol, maleic anhydride-based high molecular weight compound such as maleic anhydride-methyl vinyl ether copolymer, and sodium polyacrylate.

In the present invention, a solution in the solvent of the carbonyl group-containing compound or the hydrazide compound(C-1) having at least one carbonyl group or hydrazide group in the molecule and a solution in the solvent of the polyfunctional compound(cross-linking agent) (C-2) having at least two hydrazide groups or carbonyl groups in the molecule are separately prepared, and the water-soluble or water-swellable high molecular weight substance(D) is incorporated in at least one of such solution.

The solution in the solvent of the compound (C-1) having at least one carbonyl group or hydrazide group in the molecule is first coated on the surface of the substrate constituting the medical device, and the solution containing the polyfunctional compound (C-2) is then coated to promote the cross-linking reaction between the hydrophilic high molecular weight compound and the cross-linking agent to thereby promote the formation and insolubilization of the interpenetrating network of the reaction product (the cross-linked product) and the water-soluble or water-swellable high molecular weight substance (D) on the substrate surface. The water-soluble or water-swellable high molecular weight substance (D) is thereby firmly immobilized, and the medical device exhibits lubricity when it is brought in contact with an aqueous medium such as a body fluid and physiological saline.

When the water-soluble or water-swellable high molecular weight substance(D) is incorporated in at least one of the solution containing the carbonyl group-containing compound and the solution containing the hydrazide compound, the step of coating the water-soluble or water-swellable high molecular weight substance on the surface of the substrate and the step of coating the carbonyl group-containing compound or the hydrazide compound on the surface of the substrate can be accomplished in one step, and the production procedure can be simplified.

The solvent used for the dissolution of the carbonyl group-containing compound and the solvent used for dissolution of the hydrazide compound are not particularly limited, and the solvent can be adequately selected depending on the type of the material constituting the substrate of the medical device from the solvents including the proton-donating solvents which could not be employed in conventional reactions involving the isocyanate. For example, an organic solvent containing water can be used for dissolution of the hydrophilic high molecular weight compound and the cross-linking agent, and the substrate surface can be coated with the solution to promote the cross-linking reaction. However, the solvent used for dissolution of the compound (C-2) which functions as the cross-linking agent among the carbonyl group-containing compound and the hydrazide compound is preferably a solvent which does not substantially swell the substrate.

The conditions for the reaction between the carbonyl group-containing compound and the hydrazide compound are not particularly limited as long as the pH of the reaction system is on the acidic side (pH<7) since the reaction is promoted in such range, and the pH is preferably adjusted to the range of up to 5, and more preferably, to the range of up to 3 for completion of the cross-linking reaction in a short period. On the other hand, use of a solution having a pH near 7 is preferable for the handling convenience of the solution, and in addition, the copolymer used in the reaction is preferably a copolymer which preliminarily contains an anionic monomer such as acrylic acid. These reaction conditions are not particularly limited, and the reaction conditions should be adequately selected depending on the pH of the reaction system, the specific procedure employed, and the reaction time.

In the present invention as described above, a water-soluble physiologically active substance can be incorporated in the surface lubrication layer for retention of the physiologically active substance in the surface lubrication layer or for slow release of the physiologically active substance from the surface lubrication layer. Exemplary water-soluble physiologically active substances include antithrombogenic substances such as heparin, low molecular weight heparin, dermatan sulfate, heparan sulfate, activated protein C, hirudin, aspirin, thrombomodulin, DHG, plasminogen activator, streptokinase, urokinase, aprotinin, nafamostat mesylate (FUT), and gabexate mesylate (FOY); antibacterial reagent such as penicillin N, cephalosporin C, cephabacin, kanamycin, gentamycin, neomycin, chlorhexidine hydrochloride (Hibitane), and polymyxin; nucleic acids such as DNA and RNA; polysaccharides such as arginic acid, hyaluronic acid and chitosan; and proteins such as collagen and albumin.

Such physiologically active substance can be incorporated in the surface lubricating layer by incorporating the water-soluble physiologically active substance in at least either one of the solution containing the carbonyl group-containing compound or the solution containing the hydrazide compound, and coating the substrate surface with the solution; or alternatively, by preparing a solution of the water-soluble physiologically active substance in an adequate solvent separately from the solution containing the carbonyl group-containing compound and the solution containing the hydrazide compound and coating the substrate with the solution of the physiologically active substance independently from the coating with the solution containing the carbonyl group-containing compound and the solution containing the hydrazide compound.

In the present invention, a substance soluble in an aqueous solvent can be used for the cross-linking agent, and use of such cross-linking agent enables incorporation of water-soluble physiologically active substance in the solution of the cross-linking agent in the aqueous solvent and coating of the substrate surface with such solution. As a consequence, the step of coating the substrate surface with the cross-linking agent and the step of coating the substrate surface with the physiologically active substance can be accomplished in the same step, and a surface having physiological activity in addition to the wet surface lubricity can be realized in a simple procedure.

The material used for the substrate constituting the medical device is not particularly limited in the present invention, and exemplary materials include high molecular weight materials such as polyolefins, modified polyolefins, polyethers, polyurethanes, polyamides, polyimides, polyesters, and copolymers thereof, metal materials, and ceramic materials. The substrate is not limited to the article molded by using one of the materials as described above alone, and the substrate may also comprise an article molded from a blend or an alloy of the material as described above as well as a multi-layered molded article. However, use of a high molecular weight material is preferable at least for the material of the substrate surface when a stronger insolubilization of the hydrophilic high molecular weight compound is to be attained by swelling the substrate with the solvent, since the high molecular weight material has higher susceptibility to swelling by the solvent.

Typical examples of the medical device of the present invention are catheters and guidewires. Other exemplary medical devices include:

1) catheters orally or nasally inserted/indwelled in digestive apparatus such as gastric catheter, feeding catheter, and elementary diet (ED) tube;
2) catheters orally or nasally inserted/indwelled in respiratory tract or trachea such as oxygen catheter, oxygen canule, tube and cuff of endotracheal tube, tube and cuff of tracheotomy tube, and endotracheal suction catheter;
3) catheters inserted/indwelled in urethra or ureter such as urethral catheter, ureteral catheter, and balloon or catheter of balloon catheter;
4) catheters inserted/indwelled in various body cavity, organ or tissue such as suction catheter, drainage catheter, and rectal catheter;
5) catheters inserted/indwelled in blood vessel such as indwelling catheter, IVH catheter, thermodilution catheter, angiography catheter, and vascular dilatation catheter and dilator or introducer; and guidewire and stylet used in combination with such catheter;
6) analytical and therapeutical device to be inserted in various organs, contact lens, etc.;
7) stents, artificial blood vessel, artificial trachea, artificial bronchus, etc.; and
8) medical device for use in extracorporeal circulation (artificial heart, oxygenator, artificial kidney, etc.) and their circuits.

EXAMPLES

Next, the present invention is described in further detail by referring to the Examples of the present invention which by no means limit the scope of the invention.

Example 1

24. 6 g of dimethylacrylamide (DMAA), 0. 4 g of diacetone acrylamide (DAAAm), and 0.005 g of azobisisobutylonitrile (AIBN) were polymerized by using 100 g of 1,4-dioxane which had been subjected to $N_2$ bubbling for 1 hour for the solvent and in the presence of $N_2$ at 75° C. for 6 hours with stirring. The solution after the polymerization was purified by repeating the reprecipitation in n-hexane for 3 times, and the product was dried under reduced pressure to obtain a random copolymer.

A sheet of polyurethane (Miractran E998PNAT manufactured by Japan Miractran) was immersed in 5 wt % solution of this random copolymer in tetrahydrofuran (THF) for 15 seconds. The sheet taken out of the solution was dried at 60° C. for 2 hours, and then immersed in 1.0 wt % aqueous solution of carbohydrazide adjusted to pH 3.0 for 3 seconds to promote cross-linking reaction, and dried.

The resulting sheet having the hydrophilic polymer insolubilized on its surface exhibited excellent lubricity when the sheet was wetted with physiological saline or water. The sheet also exhibited excellent lubricity in the slidability test as described below, and no deterioration in the performance was noticed in the slidability test.

Example 2

29.7 g of triethylene glycol was added dropwise to 72.3 g of sebacic dichloride at 50° C., and hydrogen chloride was removed under reduced pressure for 3 hours at 50° C. To 22.5 g of the resulting oligoester was added 4.5 g of methyl ethyl ketone, and the mixture was added dropwise to a solution of 5.0 g of sodium hydroxide, 6.93 g of 31% hydrogen peroxide, 0.44 g of dioctyl phosphate (surfactant), and 120 g of water, and the reaction was allowed to take place at −5° C. for 20 minutes. The resulting product was repeatedly washed with water and methanol and dried to obtain a polyperoxide (PPO) having two or more peoxide groups in the molecule.

Next, 10 g of this PPO was used for the polymerization initiator in the polymerization of 90 g of diacetone acrylamide (DAAAm) in the solvent of 1,4-dioxane by stirring the solution at 80° C. for 30 minutes in the presence of $N_2$. The reaction product was reprecipitated in hexane to obtain polyDAAAm having peoxide group in the molecule. Next, 0.5 g of this polyDAAAm was used for the polymerization initiator, and 24.5 g of dimethylacrylamide (DMAA) in 100 g of 1,4-dioxane was polymerized at 80° C. for 6 hours to obtain a block copolymer comprising the reactive domain of polyDAAAm and the water-swellable hydrophilic domain of polyDMAA.

A sheet of polyurethane (Miractran E998PNAT manufactured by Japan Miractran) was immersed for 15 seconds in 5 wt % solution of this block copolymer in tetrahydrofuran (THF), and the sheet was then removed from the solution. After drying the sheet at 60° C. for 2 hours, the sheet was immersed in 1.0 wt % aqueous solution of carbohydrazide adjusted to pH 3.0 for 3 seconds to promote cross-linking reaction, and dried.

The resulting sheet having the hydrophilic copolymer insolubilized thereto exhibited excellent lubricity when wetted with physiological saline or water. This sheet also exhibited excellent lubricity in the slidability test as described below, and no deterioration in its performance was noticed in the test.

Comparative Example 1

The polyurethane sheet which is the same as the one used in Example 1 was immersed for 15 seconds in 5 wt % solution of the block copolymer synthesized in Example 2 in tetrahydrofuran (THF). The sheet was then removed from the solution, and dried at 60° C. for 2 hours. The resulting sheet exhibited lubricity for a while when wetted with physiological saline or water. The sample sheet, however, exhibited no lubricity after the slidability test as described below indicating the low abrasion resistance.

Example 3

A solution of 5 wt % of the random copolymer synthesized in Example 1 and 2.5 wt % of polyurethane (adhesive polyurethane PANDEX T-5210 manufactured by Dainippon Ink & Chemicals, Inc.) in tetrahydrofuran (THF) was prepared. A sheet of polyethylene (VLDPE Lumitack 12-1 manufactured by Tosoh Corp.) was immersed for 1 minutes in this solution, and the sheet was then removed from the solution. After drying the sheet at 60° C. for 2 hours, the sheet was immersed in 1.0 wt % aqueous solution of carbohydrazide adjusted to pH 3.0 for 3 seconds to promote cross-linking reaction, and dried.

The resulting polyethylene sheet having the hydrophilic copolymer insolubilized thereto exhibited excellent lubricity when wetted with physiological saline or water. This sheet also exhibited excellent lubricity in the slidability test as described below, and no deterioration in its performance was noticed in the test.

Example 4

A solution of 5 wt % of the random copolymer synthesized in Example 1 and 2.5 wt % of polyvinyl pyrrolidone (K-90 manufactured by Wako Pure Chemicals; average molecular weight (Mw), 1,200,000) in $CHCl_3$ was prepared. A sheet of polyurethane (Tecoflex EG-65D manufactured by Nippon Surmedics) was immersed for 15 seconds in this solution, and the sheet was then removed from the solution. After drying the sheet at 60° C. for 2 hours, the sheet was immersed in 1.0 wt % aqueous solution of carbohydrazide adjusted to pH 3.0 for 3 seconds to promote cross-linking reaction, and dried.

The resulting sheet having the hydrophilic copolymer insolubilized thereto exhibited excellent lubricity when wetted with physiological saline or water. This sheet also exhibited excellent lubricity in the slidability test as described below, and no deterioration in its performance was noticed in the test.

Comparative Example 2

A solution of 5 wt % of the random copolymer synthesized in Example 1 and 2.5 wt % of polyvinyl pyrrolidone (K-90 manufactured by Wako Pure Chemicals; average molecular weight (Mw), 1,200,000) in $CHCl_3$ was prepared. A sheet of polyethylene (VLDPE Lumitack 12-1 manufactured by Tosoh Corp.) was immersed for 1 minutes in this solution, and the sheet was then removed from the solution and dried at 60° C. for 2 hours.

The resulting polyethylene sheet exhibited lubricity for a while when wetted with physiological saline or water. The sheet, however, exhibited no lubricity after the slidability test as described below, confirming the low abrasion resistance.

Example 5

22.0 g of dimethylacrylamide (DMAA), 0.5 g of diacetone acrylamide (DAAAm) and 2.5 g of 2-ethylhexylacrylate (2-EHA), and 0.005 g of azobisisobutyronitrile (AIBN) were polymerized at 75° C. for 6 hours with stirring in the presence of $N_2$ and in the solvent of 100 g of 1,4-dioxane which had been subjected to $N_2$ bubbling for 1 hour. The solution after the polymerization was purified for three times by reprecipitation in n-hexane, and dried under reduced pressure to obtain a random copolymer.

A sheet of polyethylene (VLDPE Lumitack 12-1 manufactured by Tosoh Corp.) was immersed for 1 minutes in the solution of 5 wt % of this random copolymer in tetrahydrofuran (THF), and the sheet was then removed from the solution. After drying the sheet at 60° C. for 2 hours, the sheet was immersed in 1.0 wt % aqueous solution of carbohydrazide adjusted to pH 3.0 for 3 seconds to promote cross-linking reaction, and dried.

The resulting sheet exhibited excellent lubricity when wetted with physiological saline or water. This sheet also exhibited excellent lubricity in the slidability test as described below, and no deterioration in its performance was noticed in the test.

Example 6

24.5 g of dimethylacrylamide (DMAA), 0.5 g of diacetone acrylamide (DAAAM) and 0.05 g of acrylic acid (AA), and 0.005 g of azobisisobutyronitrile (AIBN) were polymerized at 75° C. for 6 hours with stirring in the presence of $N_2$ and in the solvent of 100 g of 1,4-dioxane which has been subjected to $N_2$ bubbling for 1 hour. The solution after the polymerization was purified for three times by reprecipitation in n-hexane, and dried under reduced pressure to obtain a random copolymer.

A sheet of polyurethane (Miractran E998PNAT manufactured by Japan Miractran) was immersed for 15 seconds in a solution of 5 wt % of this random copolymer in tetrahydrofuran (THF), and the sheet was then removed from the solution. After drying the sheet at 60° C. for 2 hours, the sheet was immersed in 1.0 wt % aqueous solution of carbohydrazide adjusted to pH 3.0 for 3 seconds to promote cross-linking reaction, and dried.

The resulting sheet having the hydrophilic copolymer insolubilized thereto exhibited excellent lubricity when wetted with physiological saline or water. This sheet also exhibited excellent lubricity in the slidability test as described below, and no deterioration in its performance was noticed in the test.

Example 7

A 5 wt % solution in tetrahydrofuran (THF) of the random copolymer synthesized in Example 1 was prepared. A tube of polyurethane (Tecoflex EG-65D manufactured by Nippon Surmedics) was immersed for 15 seconds in this solution, and the tube was then removed from the solution. After drying the sheet at 60° C. for 2 hours, the tube was immersed in 1.0 wt % aqueous solution of carbohydrazide adjusted to pH 3.0 supplemented with 1 wt % of heparin sodium (manufactured by Wako Pure Chemicals) for 3 hours to promote cross-linking reaction, and dried.

The resulting tube having the hydrophilic copolymer insolubilized thereto exhibited excellent lubricity when wetted with physiological saline or water. This tube exhibited no adhesion of thrombosis when the tube was indwelled in rabbit femoral vein for two weeks. Formation of a lubricious, antithrombogenic surface in the tube has been confirmed by these results.

Slidability Test

The sliding resistance was measured by using a creep meter manufactured by YAMADEN K.K. (RHEONER RE-33005) using the jig for friction and abrasion test manufactured by the same manufacturer (FW-3305-1). The measurement was conducted for the sample sheet wetted with water, and under the load of 200 g weight. The slidability test was conducted for each sample sheet at a test speed of 10 mm/sec. and a test width of 20 mm for 50 cycles to compare the value of resistance at the start of the test and the value at the end of the test. The results are shown in Table 1, below.

TABLE 1

|  | Sliding resistance (gf) | |
| --- | --- | --- |
|  | Before the test | After the test |
| Example 1 | 12 | 12 |
| Example 2 | 15 | 15 |
| Comp. Example 1 | 26 | 59 |
| Example 3 | 19 | 19 |
| Example 4 | 15 | 15 |
| Comp. Example 2 | 20 | 38 |
| Example 5 | 15 | 15 |
| Example 6 | 12 | 12 |

MERITS OF THE INVENTION

As described above, the medical device and its production method according to the present invention has enabled to incorporate a hydrophilic polymer in the surface of the substrate of the medical device in firm, chemically stable manner. The medical device of the present invention is free from the phenomenon of detachment, delamination, or dissolution of the coating from the material surface as found in the methods of coating vegetable oils or other synthetic oils on the material surface. Accordingly, high safety is reliably realized in the present invention.

The present invention has also enabled to accomplish the surface lubrication treatment without using the highly reactive proton-accepting functional group such as isocyanate group. This, in turn, has enabled use of a proton-donating solvent, and strict moisture control in the working area became unnecessary. As a consequence, the surface lubrication treatment can be accomplished under moderate conditions with no loss in the physical properties inherent to the substrate material. In view of such situation, no substantial limitation is imposed on the type of the material used for the substrate, and the surface lubrication treatment can be accomplished for a wide variety of medical device.

The medical device of the present invention has enabled to reduce the surface frictional resistance of the medical device to an extremely low level especially when the medical device is wetted by a body fluid such as saliva, digestive fluid, or blood, or with an aqueous liquid such as physiological saline or water. Accordingly, the medical device of the present invention enjoys the merits of ease of insertion, reduced pain of the patient, prevention of the damage in the mucous membrane or inner membrane of the blood vessel, and the like when used as a guidewire, catheter, and the like.

In addition, the present invention has the.merit that surface lubrication treatment can be accomplished in the presence of a water-soluble physiologically active substance such as heparin, and that the material surface can be simultaneously imparted with physiological activity (such as antithrombogenicity).

What is claimed is:

1. A medical device having a surface exhibiting lubricity with wet wherein the medical device has a surface lubrication layer formed on the substrate constituting the medical device, and said surface lubrication layer comprises a reaction product of a hydrophilic high molecular weight compound having at least one selected from a group consisting of a carbonyl group and a hydrazine residue in the molecule and a cross-linking agent having at least two carbonyl groups or hydrazine residues which are capable of reacting with the carbonyl group or the hydrazine residue in one molecule.

2. The medical device according to claim 1 wherein said hydrophilic high molecular weight compound has at least one carbonyl group in the molecule and the cross-linking agent has at least two hydrazine residues in one molecule.

3. The medical device according to claim 1 wherein said surface lubrication layer further comprises a water-soluble or water-swellable high molecular substance.

4. The medical device according to claim 1 wherein said cross-linking agent is soluble in an aqueous solvent.

5. The medical device according to claim 1 wherein said surface lubrication layer further comprises a water-soluble physiologically active substance.

6. A medical device having a surface exhibiting lubricity with wet wherein the medical device has a surface lubrication layer formed on the substrate constituting the medical device, and said surface lubrication layer has an interpenetrating network comprising a reaction product of a carbonyl group-containing compound having at least one carbonyl group in the molecule with a hydrazide compound having at least two hydrazine residues in one molecule and a water-soluble or water-swellable high molecular weight substance.

7. A medical device having a surface exhibiting lubricity with wet wherein the medical device has a surface lubrication layer formed on the substrate constituting the medical device, and said surface lubrication layer has an interpenetrating network comprising a reaction product of a hydrazide compound having at least one hydrazine residue in the molecule with a carbonyl group-containing compound having at least two carbonyl groups in one molecule and a water-soluble or water-swellable high molecular weight substance.

8. A method for producing a medical device having a surface exhibiting lubricity with wet comprising the steps of:
    coating the surface of the substrate constituting the medical device with a solution containing a hydrophilic high molecular weight compound having at least one carbonyl group in the molecule, and
    coating the surface with a solution containing a cross-linking agent comprising a hydrazide compound having at least two hydrazine residues in one molecule.

9. The method for producing a medical device according to claim 8 wherein at least one of said solution containing the hydrophilic high molecular weight compound and said solution containing the cross-linking agent further comprises a water-soluble or water-swellable high molecular weight substance.

10. The method for producing a medical device according to claim 8 wherein an aqueous solvent is used for the solvent of said cross-linking agent.

11. The method for producing a medical device according to claim 10 wherein said solution of said cross-linking agent in said aqueous solvent further comprises a water-soluble physiologically active substance.

12. A method for producing a medical device having a surface exhibiting lubricity with wet comprising the steps of:
    coating the surface of the substrate constituting the medical device with a solution containing a hydrophilic high molecular weight compound having at least one hydrazine residue in the molecule, and
    coating the surface with a solution containing a cross-linking agent comprising a carbonyl group-containing compound having at least two carbonyl groups in one molecule.

13. The method for producing a medical device according to claim 12 wherein at least one of said solution containing the hydrophilic high molecular weight compound and said solution containing the cross-linking agent further comprises a water-soluble or water-swellable high molecular weight substance.

14. The method for producing a medical device according to claim 12 wherein an aqueous solvent is used for the solvent of said cross-linking agent.

15. The method for producing a medical device according to claim 14 wherein said solution of said cross-linking agent in said aqueous solvent further comprises a water-soluble physiologically active substance.

16. A method for producing a medical device having a surface exhibiting lubricity with wet comprising the steps of:
   coating the surface of the substrate constituting the medical device with a solution containing a carbonyl group-containing compound having at least one carbonyl group in the molecule, and
   coating the surface with a solution containing a hydrazide compound having at least two hydrazine residues in one molecule;
wherein at least one of said solution containing the carbonyl group-containing compound and said solution containing the hydrazide compound further comprises a water-soluble or water-swellable high molecular substance.

17. A method for producing a medical device having a surface exhibiting lubricity with wet comprising the steps of:
   coating the surface of the substrate constituting the medical device with a solution containing a hydrazide compound having at least one hydrazine residue in the molecule, and
   coating the surface with a solution containing a cross-linking agent comprising a carbonyl group-containing compound having at least two carbonyl groups in one molecule;
wherein at least one of said solution containing the carbonyl group-containing compound and said solution containing the hydrazide compound further comprises a water-soluble or water-swellable high molecular substance.

* * * * *